US006200573B1

(12) United States Patent
Locke

(10) Patent No.: US 6,200,573 B1
(45) Date of Patent: Mar. 13, 2001

(54) METHOD OF MEDICAL MANAGEMENT FOR LOWER URINARY TRACT SYMPTOMS AND BENIGN PROSTATIC HYPERPLASIA

(75) Inventor: D. Russell Locke, Ocala, FL (US)

(73) Assignee: StarCor Pharmaceuticals, Inc., Ocala, FL (US)

( * ) Notice: Subject to any disclaimer, the term of this patent is extended or adjusted under 35 U.S.C. 154(b) by 0 days.

(21) Appl. No.: 09/489,183

(22) Filed: Jan. 20, 2000

Related U.S. Application Data

(60) Provisional application No. 60/168,970, filed on Dec. 3, 1999.

(51) Int. Cl.$^7$ .......................... A61K 35/78; A61K 31/505
(52) U.S. Cl. ......................................... 424/195.1; 514/254
(58) Field of Search .......................... 424/195.1; 514/254

(56) References Cited

U.S. PATENT DOCUMENTS

| | | | |
|---|---|---|---|
| 5,212,176 | 5/1993 | Kyncl et al. | 514/254 |
| 5,284,873 * | 2/1994 | Salinero-Rodero et al. | 514/558 |
| 5,294,615 | 3/1994 | Meyer et al. | 514/254 |
| 5,362,730 * | 11/1994 | Bauer et al. | 514/254 |
| 5,412,095 | 5/1995 | Morley et al. | 544/291 |
| 5,504,207 | 4/1996 | Mannino et al. | 544/291 |
| 5,508,279 | 4/1996 | Gray | 514/254 |
| 5,543,146 | 8/1996 | Perez | 424/195.1 |
| 5,753,641 | 5/1998 | Gormley et al. | 514/179 |
| 5,817,649 | 10/1998 | Labrie | 514/169 |
| 5,942,519 | 8/1999 | Waldstreicher | 514/284 |
| 5,952,351 | 9/1999 | Evans et al. | 514/321 |
| 6,039,950 * | 3/2000 | Khwaja et al. | 424/195.1 |

OTHER PUBLICATIONS

Barry et al., The American Urological Association Symptom Index for Benign Prostatic Hyperplasia, Nov. 1992, 1549–1557.
Beduschi et al., Alpha–Blockade Therapy for Benign Prostatic Hyperplasia: From A Nonselective to a more Selective Alpha Adrenergic Antagonist, Feb. 1998, 861–872.
Berry et al., The Development of Human Benign Prostatic Hyperplasia With Age, Sep. 1984, 474–479.
Caine, Alpha–Adrenergic Blockers for the Treatment of Benign Prostatic Hyperplasia, Aug. 1990, 641–649.
Carilla et al., Binding of Permixon, a New Treatment for Prostatic Benign Hyperplasia, to the Cytosolic Androgen Receptor in the Rat Prostate, 1984, 521–523.

Christensen et al., Clinical Manifestations of Benign Prostatic Hyperplasia and Indications for Therapeutic Intervention, Aug. 1990, 509–616.
di Silverio et al., Evidence that Serenoa repens Extract Displays an Antiestrogenic Activity in Prostatic Tissue of Benign Prostatic Hypertrophy Patients, 1992, 309–314.
Guess, Benign Prostatic Hyperplasia: Antecedents and Natural History, 1992, 131–153.
Jacobsen et al., Natural History of Prostatism: Risk Factors for Acute Urinary Retention, Aug. 1997, 481–487.
Lepor, Alpha–Adrenoceptor Selectivity: Clinical or Theoretical Benefit?, 1995, 57–61.
Marks, Clinical Effects of Saw Palmetto Extract in Men with Symptomatic BPH, May 4, 1999 (94$^{th}$ Annual Meeting of American Urological Association), <www.usrf.org>.
Marwick, Growing Use of Medicinal Botanicals Forces Assessment by Drug Regulators, Feb. 22, 1995, 607–609.
McConnell et al., The Effect of Finasteride on the Risk of Acute Urinary Retention and the Need for Surgical Treatment Among Men With Benign Prostatic Hyperplasia, Feb. 26, 1998, 557–563.
Overmyer, Saw Palmetto Shown to Shrink Prostatic Epithelium, Jun. 1999, 1, 42–43.
Wilson, The Testes and the Prostate, Sep. 1987, 628–629.
Wilt et al., Saw Palmetto Extracts for Treatment of Benign Prostatic Hyperplasia, Nov. 11, 1998, 1604–1609.
Benign Prostatic Hyperplasia: Diagnosis and Treatment, U.S. Dept. of Health.
Treating Your Enlarged Prostate, AHCPR Publications Clearinghouse.
Finasteride, Physicians Desk Reference, 110c–111a, 1998.
Finasteride, Physicians Desk Reference, 467–469.
Savage et al., Combination Medical Therapy for Symptomatic Benign Prostatic Hyperplasia, Aug. 1998, 578–583.

\* cited by examiner

Primary Examiner—Christopher Tate
Assistant Examiner—Michael V. Meller
(74) Attorney, Agent, or Firm—Charles D. Gunter, Jr.

(57) ABSTRACT

Disclosed is a method of medical management for men with lower urinary tract symptoms (LUTS) and benign prostatic hyperplasia (BPH), involving combination therapy of an $\alpha_1$-adrenergic antagonist, i.e., terazosin in combination with a phytotherapeutic agent, *Serenoa repens* (saw palmetto) extract. The combination provides relief from both dynamic and mechanical obstructive effects of benign prostatic hyperplasia. Therapeutic compositions useful for such treatment and pharmaceutical-nutraceutical kits containing such compositions are disclosed.

18 Claims, No Drawings

METHOD OF MEDICAL MANAGEMENT FOR LOWER URINARY TRACT SYMPTOMS AND BENIGN PROSTATIC HYPERPLASIA

CROSS-REFERENCE TO RELATED APPLICATION

Benefit is herein claimed of the filing date under 35 U.S.C. §§ 119 and/or 120, and 37 CFR § 1.78 to U.S. Provisional Patent Application Ser. No. 60/168,970, filed on Dec. 3, 1999, entitled "Method of Medical Management for Lower Urinary Tract Symptoms and Benign Prostatic Hyperplasia".

BACKGROUND OF THE INVENTION

1. Field of the Invention

This invention relates to a novel and improved method of medical management for men with lower urinary tract symptoms (LUTS) and benign prostatic hyperplasia (BPH), involving combination therapy of administering therapeutically effective amounts of an $\alpha_1$-adrenergic antagonist, i.e., terazosin in combination with a phytotherapeutic agent, *Serenoa repens* (saw palmetto) extract.

2. Description of the Prior Art

Benign prostatic hyperplasia (BPH) is a common health related condition that affects many men as they age. Histologic changes that typify BPH are present in 50% of men by age 60 and approximately 90% by age 85 (Berry S J, Coffey D S, Walsh P C, Ewing L L. The development of human benign prostatic hyperplasia with age. *J Urol.* 1984; 132:474–479). BPH has a major impact on quality of life and exacts a heavy toll upon healthcare resources, including physicians, hospitals, and surgical facilities. In the United States, treatment of BPH exceeds $2 billion in costs, accounts for 1.7 million physician office visits, (Guess H A. Benign prostatic hyperplasia antecedents and natural history. *Epidemiol Rev.* 1992; 14:131–153) and results in more than 300,000 prostatectomies annually (McConnell J D, Barry M J, Bruskewitz R C. *Benign Prostatic Hyperplasia.* Rockville, Md.: Agency for Health Care Policy and Research, Public Health Service, US Dept of Health and Human Services; 1994. Clinical Practice Guideline No. 8, AHCPR publication 94-0582).

Benign prostatic hyperplasia is a heterogeneous disorder shown in studies to be caused by hormonal factors, growth factors, stromal-epithelial interactions, and aging. It is a progressive condition, which results in increased frequency of urination, nocturia, a weak urine stream, hesitancy or delay in starting the urine flow and incomplete bladder emptying. Chronic consequences of BPH can include hypertrophy of bladder smooth muscle, a decompensated bladder, an increased incidence of urinary tract infection, urinary stone formation and renal failure.

Anatomically, the prostate is a fibromuscular and glandular organ that encircles the urethra at the bladder neck. It is situated in the true pelvis below the pubic bone and in front of the rectum. Its upper end (base) is continuous with the neck of the bladder, and its lower end (apex) rests on the pelvic floor. The urethra runs through the prostate from base to apex. The normal prostate is approximately 20 cc in size (volume) and measures between 3 and 4 cm at its widest portion; it is 4–6 cm in length and 2–3 cm in thickness. Structurally it is composed of fibromuscular tissue (30–50%) and glandular epithelial cells (50–70%). The fibromuscular component is present mostly anteriorly, while the glandular element is mostly in the posterior and lateral aspects of the organ. Anteriorly and laterally, a capsule composed of fibrous and smooth muscle tissue surrounds the prostate.

It is widely accepted that obstruction secondary to BPH occurs as a result of two factors: A dynamic component resulting from contraction of smooth muscle of the prostate and prostatic urethra mediated primarily by $\alpha$-adrenergic receptors; and a mechanical component related to the presence of a mass of hyperplastic acinar or stromal tissue, which compresses and narrows the urethral lumen (Caine M: Alpha-adrenergic blockers for the treatment of benign prostatic hyperplasia. *Urol Clin North Am* 1990; 17:641).

The ratio of epithelium to smooth muscle in the prostate can vary substantially among individual men, from 1:3 to 4:1. In general, however, larger prostates contain more androgen-dependent epithelial elements than smaller glands, which contain a higher proportion of smooth muscle. In either case, the outcome of BPH may be urethral obstruction, induced dynamically by smooth muscle contraction and mechanically by epithelial overgrowth, or by a combination of both.

After ruling out alternative causes of voiding disturbances, clinicians rely on surrogate markers to determine the presence of BPH. These include subjective assessments of lower urinary tract symptoms (LUTS) and objective measurements of flow rate and prostate volume. In 1993, the American Urological Association (AUA) developed a questionnaire to quantitate the severity of symptoms in patients with BPH (Barry M F, Fowler F J, O'Leary M P, et al, and the Measurement Committee of the American Urologic Association symptom index for benign prostatic hyperplasia. *J Urol.* 1992; 148:1549–1557). The AUA Symptom Index (AUASI) consists of seven questions related to the severity of urinary frequency, nocturia, weak urinary stream hesitancy intermittency, incomplete emptying, and urgency, each of which has a score of (0 to 5). The maximum score is therefore 35. Patients with scores of (0 to 7) are good candidates for watchful waiting with periodic reevaluation. Men with moderate (8 to 19) to severe (20 to 35) scores usually require therapy to avoid complications.

A number of methodologies can be employed to estimate prostate volume, including magnetic resonance imaging (MRI), transrectal ultrasonography (TRUS), digital rectal examination (DRE), and serum prostate specific antigen (PSA) level. DRE and PSA are by far the most practical and cost effective means of estimating prostate volume. PSA is a glycoprotein that is secreted in the cytoplasm of prostatic cells. Its function is to aid in the liquefaction of semen. Serum PSA is a useful proxy for prostate volume, according to a direct comparison of serum PSA levels and prostate volumes measured using TRUS or MRI. A strong log-log linear relationship was found between the two, although the slope of the relationship changes with advancing age. In light of these results, serum PSA may be used as a surrogate for prostate volume to identify patients with prostate enlargement over certain threshold sizes.

Epidemiological studies show that men with prostate volumes greater than 30 cc have a three fold higher risk of acute urinary retention (Jacobsen S J, Jacobson D J, Girman C J, Roberts R O, Rhodes T. Guess H A, Lieber M M. Natural History of Prostatism: Risk Factors for Acute Urinary Retention, *J Urol.* 1997; 158:481–487). Similarly, a recent clinical trial demonstrated that men with serum PSA levels greater than 1.4 ng/ml and 3.3 ng/ml were 2.0 and 4.2 times more likely to develop acute urinary retention respectively, than men with Serum PSA levels less than 1.4 ng/ml (McConnell J D, Bruskewitz R, Walsh P, et al for the PROSCAR Long-Term Efficacy and Safety Study (PLESS) Group. The effect of finasteride on the risk of acute urinary retention and the need for surgical treatment among men with benign prostatic hyperplasia. N Engl J Med. 1998; 338(9): 557–563).

Estimations of prostate volume, either by DRE or serum PSA level, may be used to appropriately guide the selection of therapeutic alternatives, particularly when a goal of therapy is reduction of the risk for disease progression, development of urinary retention, and the need for BPH related surgery.

Treatment options for BPH include lifestyle modification, device, surgery, pharmacologic, and phytotherapeutic interventions. There are two classes of pharmacologic intervention: α-antagonists, which act via adrenergic pathways, and 5α-reductase inhibitors, which act via hormonal mechanisms. Alpha-Antagonists can be effective in relieving symptoms of BPH, whereas the 5α-reductase inhibitors have been shown to reduce prostate volume. Serenoa repens (saw palmetto) extract, a popular phytotherapeutic agent, has been shown to reduce prostate volume and to a lesser extent relieve symptoms and improve urine flow.

The therapeutic rationale for α-adrenergic blockade is two fold. A very large percentage of the hyperplastic prostate gland, at least 40% is comprised of smooth muscle, and that smooth muscle has a very high density of α-adrenergic receptors (Lepor H. $α_1$-adrenoceptor selectivity: clinical or theoretical benefit? Br J Urol. 1995; 76 9 suppl. 1): 57–61). The sympathetic nervous system mediates the tension of prostatic muscle tissue via adrenergic receptors, specifically, the $α_1$-adrenoceptors. Therefore, adrenoceptor stimulation is thought to be capable of increasing smooth muscle tone in the prostate, thereby placing constrictive pressure on the prostatic urethra and bladder neck, which induces obstructive symptoms (Beduschi M C, Beduschi R, Osterling J E. Alpha-blockade therapy for benign prostatic hyperplasia: from a nonselective to a more selective $α_{1A}$-adrenergic antagonist. Urology. 1998; 51:861–872). The mechanism of action of $α_1$-antagonists presumably is to relax prostatic smooth muscle and, thus, relieve the obstructive symptoms characteristic of moderate to severe BPH.

Three synthetic pharmocologic $α_1$-adrenergic antagonists have been approved by the FDA for the treatment of the symptoms of BPH e.g. terazosin (Hytrin®), doxazosin (Cardura®), and tamsulosin (Flomax®). These 3 agents provide prompt relief of symptoms, but do not alter prostate size.

The role of androgens in the development of benign prostatic hyperplasia in men is well documented (Wilson, N. Engl. J. Med. 317: 628–629, 1987). The enlargement of the prostate gland is dependent on the potent androgen, 5α-dihydrotestosterone (DHT). Luteinizing hormone-releasing hormone stimulates the pituitary gland to release luteinizing hormone, which stimulates the testes to produce testosterone (95% of which is produced by the testes). In the prostate cell, testosterone is converted to its more active metabolite 5α-dihydrotestosterone (DHT), by the enzyme Type II 5α-reductase. Then (DHT) binds to the cytoplasmic androgen receptor and the complex enters the cell's nucleus where it activates transcription of androgen-dependent genes.

Finasteride (sold under the trademark Proscar®) is a competitive and specific inhibitor of Type II 5α-reductase with which it slowly forms a stable enzyme complex. Finasteride has no affinity for the androgen receptor. Lowering of DHT leads to shrinkage of the enlarged prostate gland in most men (17.9% reduction of total prostate volume) compared to subjects receiving placebo. This can lead to gradual improvement of symptoms and urine flow over the next several months. Finasteride has also been shown to reduce the risk of acute urinary retention and the need for BPH-related surgery by 57% and 55%, respectively (McConnell J D, Bruskewitz R, Walsh P, et al for the PROSCAR Long-Term Efficacy and Safety Study (PLESS) Group. The effect of finasteride on the risk of acute urinary retention and the need for surgical treatment among men with benign prostatic hyperplasia. N Engl J Med. 1998; 338(9): 557–563).

The usefulness of finasteride has been somewhat limited due to a multitude of undesirable side effects including impotence, decreased libido, ejaculatory disorders, and breast enlargement and tenderness (Agency for Health Care Policy and Research (AHCPR), "Treating Your Enlarged Prostate," AHCPR Publication No. 940584, 1994). Furthermore, finasteride causes a decrease in serum prostate specific antigen (PSA) levels by approximately 50% in patients with BPH, even in the presence of prostate cancer. This lowering of serum PSA levels may obscure its utility as a tumor marker for prostate cancer (Facts and Comparisons, Finasteride monograph, St. Louis, Mo.: Facts and Comparisons, Inc. 1999).

The use of phytotherapeutic agents, also known as plants or plant extracts, for the treatment of symptomatic BPH has been growing steadily throughout the world. In some European countries, plant extracts are the most commonly recommended initial treatment for men with obstructive voiding symptoms secondary to BPH. Serenoa repens (saw palmetto) is the most extensively studied phytotherapeutic agent used to treat lower urinary tract symptoms (LUTS) and BPH.

Saw palmetto extracts are derived from the dried ripe fruit of the American dwarf palm tree, Serenoa repens (also known by its botanical name Sabal serrulata) which is indigenous to the southeastern United States. The liposterolic extract of the Serenoa repens berry is comprised of a complex mixture of phytosterols and fatty acids. The mechanism of action of Serenoa repens is not known but may include alteration of cholesterol metabolism (Christensen M M, Bruskewitz R C. Clinical manifestations of benign prostatic hyperplasia and the indications for therapeutic intervention. Urol. Clin. North Am. 1990; 17:509–516), antiestrogenic, antiandrogenic, and anti-inflammatory effects (Marwick C. Growing use of medicinal botanicals forces assessment by drug regulators. JAMA. 1995; 273:607–609), and a decrease in available sex hormone-binding globulin (DiSilverio F. D'Eramo G, Lubrano C, et al. Evidence that Serenoa repens extract displays an antiestrogenic activity in prostate tissue of benign prostatic hypertrophy patients. Eur Urol. 1992; 21:309–314). Animal studies have shown that liposterolic extracts of Serenoa repens inhibit competitively the binding to the cytosolic androgen receptor in prostate cells (Carilla E, et al. Binding of Permixon, A New Treatment For Prostatic Benign Hyperplasia, To The Cytosolic Androgen Receptor In The Rat Prostate. J Steroid Biochem, 1984; 20.1:521–523). These findings suggest that the beneficial effects observed in human trials may be a result of a direct action at the cytosolic androgen receptor.

A systematic review and quantitative meta-analysis of 18 randomized controlled trials involving 2939 men concluded that extracts from the saw palmetto plant, Serenoa repens improves urinary tract symptoms and flow measures in men with BPH. Furthermore, compared with finasteride, *Serenoa repens* produces similar improvements in urinary tract symptoms and flow measures, has fewer adverse treatment effects, and costs less (Wilt T J, et al. Saw Palmetto Extracts for Treatment of Benign Prostatic Hyperplasia. *JAMA.* 1998; 280:1604–1609.

A recent randomized double blind clinical trial examining the safety, efficacy, and mechanism of action of saw palmetto extract in men with symptomatic BPH demonstrated significant prostate epithelial atrophy (41% reduction of Transition Zone) compared to subjects receiving placebo. There were no significant adverse side effects or alterations in serum hormone or prostate specific antigen (PSA) levels (Marks L S. Clinical Effects of Saw Palmetto Extract in Men with Symptomatic BPH. American Urological Association 94th Annual Meeting. Dallas, Tex. May 4, 1999).

The primary benefits of treatment of BPH are: (1) improvement of symptoms, and (2) avoiding the harms of untreated disease. The two primary criterions for determining therapy for men with uncomplicated BPH are the American Urological Association (AUA) Symptom Score and prostate volume. Until recently, the risks of untreated BPH were difficult to define. However, epidemiologic data now demonstrates a clear correlation between prostate size and risks. These findings should have a significant impact on the long-term management of BPH.

It has become increasingly clear that matching each patient with the correct therapeutic agent or combination of agents can maximize the effectiveness of medical management of lower urinary tract symptoms and BPH. The evidence now suggests that patients with moderate to severe symptoms and smaller prostates (estimated volume less than or equal to 30 cc or serum PSA less than or equal to 1.4 ng/ml) are more likely to benefit from monotherapy with $\alpha_1$-adrenergic antagonists, while those with comparable symptoms and larger prostates (estimated volume >30 cc or serum PSA >1.4 ng/ml) may derive more durable results from combination therapy with an $\alpha_1$-adrenergic antagonist which acts upon the smooth muscle of the prostate alleviating the dynamic component of obstruction and an agent which reduces prostate size thereby addressing the mechanical component of obstruction.

U.S. Pat. No. 5,753,641 discloses a method of treatment for BPH involving combination therapy of a 5$\alpha$-reductase inhibitor, finasteride (Proscar®), and an $\alpha_1$-adrenergic antagonist, i.e., terazosin.

The efficacy of combination therapy was recently validated in a 1-year study of combination therapy with terazosin and finasteride in men with "large prostates" (mean volume 46.8 cc) which demonstrated favorable results (Savage S, Spungen A, Galea G, Britanico J, Vapnek J. Combination medical therapy for symptomatic BPH. *Can J Urol.* In press, 1998). The symptom scores improved by almost an additional 2 units over those of the terazosin-alone arm; this difference was statistically significant (P<0.05).

Despite these findings, combination therapy including finasteride is infrequently used in the medical management of BPH. This reality is primarily due to the troublesome adverse effects related to finasteride i.e. impotence, decreased libido, ejaculatory disorders, and breast enlargement and tenderness. Furthermore, serum PSA levels are lowered by 50% thereby obscuring its utility as a tumor marker for prostate cancer.

The above-mentioned U.S. Pat. No. 5,753,641 is disadvantageous since the 5$\alpha$-reductase inhibitor component, finasteride (Proscar®), has an unfavorable adverse effect profile.

What would be particularly desirable in the art is a combination therapy both to treat the dynamic and mechanical obstructive effects of the BPH, while avoiding the adverse effects associated with the 5$\alpha$-reductase inhibitor, finasteride (Proscar®).

SUMMARY OF THE INVENTION

The present invention provides a method of medical management for lower urinary tract symptoms (LUTS) and benign prostatic hyperplasia (BPH) in a subject susceptible thereto by administering an $\alpha_1$-adrenergic antagonist, i.e., terazosin in combination with a phytotherapeutic agent, *Serenoa repens* (saw palmetto) extract, wherein the combination therapy synergistically provides relief from both dynamic and mechanical obstructive effects of the disease.

It is an objective of the invention to provide combination therapy having increased effectiveness in preventing, slowing or reversing the effects of benign prostatic hyperplasia.

It is another object of the invention to provide therapy for lower urinary tract symptoms and BPH having significantly reduced frequency of unwanted side effects.

In another aspect, the invention provides a novel pharmaceutical composition which is effective, in and of itself, for utilization in a beneficial combination therapy because it includes a plurality of active ingredients which when administered to a patient, result in a combination therapy of the invention.

The invention further provides a pharmaceutical-nutraceutical kit for treatment of BPH, said kit including two separate containers of different active ingredients which, when administered contemporaneously, result in a combination therapy in accordance with the invention.

The invention contemplates that any of the active ingredients discussed herein may be utilized in combination with diluents and other carriers, for oral or parenteral administration, or may be delivered by any conventional delivery system. In certain preferred embodiments, active ingredients necessary to a combination therapy described above may be combined in a single pharmaceutical composition for simultaneous administration.

Additional objects, features and advantages will be apparent in the written description which follows.

DETAILED DESCRIPTION OF THE INVENTION

The present invention encompasses a method of medical management of lower urinary tract symptoms (LUTS) and benign prostatic hyperplasia (BPH) in a male subject in need of such treatment by administering therapeutically effective amounts of an $\alpha_1$-adrenergic antagonist in combination with *Serenoa repens* (hereinafter saw palmetto) extract or pharmaceutical composition thereof. The active compounds may be administered together or in any order, as described hereinafter.

By the term "patient" and/or "patients in need of such treatment" is meant male patients with moderate (AUASI Score 8–19) to severe symptoms (AUASI Score 20–35) as determined by the American Urologic Association Symptom Index (AUASI) (Barry M F, Fowler F J, O'Leary M P, et al, and the Measurement Committee of the American Urologic Association symptom index for benign prostatic hyperplasia. *J Urol.* 1992; 148:1549–1557) and prostate gland enlargement in excess of 30 cc as estimated by digital rectal examination (DRE) or serum PSA levels greater than 1.4 ng/ml.

The use of therapeutically effective amounts of the $\alpha_1$-adrenergic antagonist and saw palmetto extract in accordance with this invention effectively treats both the dynamic component of obstruction resulting from contraction of smooth muscle of the prostate and prostatic urethra mediated primarily by $\alpha_1$-adrenergic receptors; and the mechanical component of obstruction related to the presence of a mass of hyperplastic acinar or stromal tissue, which compresses and narrows the urethral lumen (Caine M: Alpha-adrenergic blockers for the treatment of benign prostatic hyperplasia. Urol Clin North Am 1990; 17:641).

The method of the invention comprises the administration of a therapeutically effective amount of an $\alpha_1$-adrenergic antagonist in synergistic combination with a therapeutically effective amount of saw palmetto extract, wherein the $\alpha_1$-adrenergic antagonist is administered to alleviate symptoms of benign prostatic hyperplasia, and the saw palmetto is administered to reduce the volume of the patient's prostate caused by the benign prostatic hyperplasia. The administration can be either oral or parenteral.

The $\alpha_1$-adrenergic antagonist is selected from a group consisting of terazosin, doxazosin, and tamsulosin. There are several different ways, described in more detail below, in which the therapeutic drug combination can be packaged or contained. The $\alpha_1$-adrenergic antagonist can be compounded into a single oral unit with the saw palmetto extract, wherein the single oral unit is a tablet or a capsule. The $\alpha_1$-adrenergic antagonist can also be dissolved or suspended in saw palmetto extract oil. The dissolved or suspended $\alpha_1$-adrenergic antagonist is then placed in a single oral softgelatin capsule.

The $\alpha_1$-adrenergic antagonist can also be formed into a first single oral unit, while the saw palmetto can be formed into a second single oral unit. Any number of first single oral units can be placed in a first container, and any number of the second single oral units can be placed in a second container. The quantity of the $\alpha_1$-adrenergic and saw palmetto can be varied per each unit as well. Further, the first and second containers can be packaged together.

Clinical studies have demonstrated that the dynamic component of obstruction due to BPH contributes to symptom severity, whereas the mechanical component of obstruction contributes to both symptom severity and the risk of disease progression i.e., urinary retention and the need for BPH related surgery (Jacobsen S J, Jacobson D J, Girman C J, Roberts R O, Rhodes T, Guess H A, Lieber M M. Natural History of Prostatism: Risk Factors for Acute Urinary Retention. J Urol. 1997; 158:481–487; McConnell J D, Bruskewitz R, Walsh P, et al for the PROSCAR Long-Term Efficacy and Safety Study (PLESS) Group. The effect of finasteride on the risk of acute urinary retention and the need for surgical treatment among men with benign prostatic hyperplasia. N Engl J Med. 1998; 338(9): 557–563).

It has been shown that stimulation of $\alpha_1$-adrenoreceptors contributes to the obstruction of benign prostatic hyperplasia (M. Caine, et al., Br. J. Urol., Vol. 48, pp. 255–263 (1976). The sympathetic nervous system mediates the tension of prostatic smooth muscle tissue via adrenergic receptors, specifically, the $\alpha_1$-adrenoceptors. Therefore, adrenoceptor stimulation is thought to increase smooth muscle tone in the prostate, thereby placing constrictive pressure on the prostatic urethra and bladder neck, which induces obstructive symptoms (Beduschi M C, Beduschi R, Osterling J E. Alpha-blockade therapy for benign prostatic hyperplasia: from a nonselective to a more selective $\alpha_1$-adrenergic antagonist. Urology. 1998; 51:861–872). The mechanism of action of $\alpha_1$-antagonists presumably is to relax prostatic smooth muscle and, thus, relieve the obstructive symptoms characteristic of moderate to severe BPH.

Examples of preferred $\alpha_1$-adrenergic receptor antagonists are terazosin (Abbott-Hytrin®) whose chemical name is 1-(4-amino-6, 7-dimethoxy-2-quinazo-linyl)-4-[(tetrahydro-2-furanyl) carbonyl]piperazine, as described in German Patent 2,646,186 and U.S. Pat. No. 4,026,894; doxazosin (Pfizer-Cardura®) whose chemical name is 1-(4-amino-6,7-dimethoxy-2-quinazolinyl)-4-[(2,3-dihydro-1,4-benzodioxin-2-yl)carbonyl]piperazine, as described in German Patent 2,847,623 and U.S. Pat. No. 4,188,390; and tamsulosin (Boehringer Ingelheim-Flomax®) whose chemical name is (-)-(R)-5-[2-[[2-(0-ethoxyphenoxy)ethyl] amino]propyl]-2-methoxybenzenesulfonamide, monohydrochloride, as described in U.S. Pat. Nos.: 4,703, 063; 4,772,475; 4,731,478; and 4,868,216, herein incorporated by reference. Serenoa repens (saw palmetto) berries contain an oil with a variety of fatty acids and phytosterols. These fatty acids include capric, caprylic, caproic, lauric, stearic, cis-linoleic, linolenic, myristic, palmitic, and oleic acid and their ethyl esters. The major phytosterols are beta-sitosterol, stigmasterol, cycloartenol, lupeol, lupenone, and 24-methyl-cycloartenol.

A typically suitable saw palmetto extract is a well-defined purified fat-soluble extract containing between 85% and 95% fatty acids and 0.2% and 0.4% phytosterol content.

Each of the $\alpha_1$-adrenergic antagonists described above in the present invention can be used to treat BPH in combination with saw palmetto extract oral, parenteral or topical administration. In this invention, the $\alpha_1$-adrenergic antagonist and the saw palmetto extract are administered in combination separately or as one single combined pharmaceutical composition via parenteral or oral means. Preferably the $\alpha_1$-adrenergic antagonist and saw palmetto extract are administered orally as separate compositions.

The amount of each component administered is determined by the attending clinicians taking into consideration the prostate volume and symptom severity of the disease, the patient's general condition and age, the potency of each component and other factors.

The $\alpha_1$-adrenergic antagonist compositions are generally administered in accordance with the current Physician's Desk Reference (PDR). (Medical Economics Co. Inc. of Oradell, N.J. 07649 53 edition, 1999). For example, terazosin is administered in a dosage range of about 1 mg to 10 mg once per day. However, larger doses are may also be suitable for some patients, depending on the symptoms and the patient's general condition, etc.

Saw palmetto extract is generally administered in a dosage of about 320 mg per day in accordance with the current Physician's Desk Reference (PDR) for Herbal Medicine ($1^{st}$ edition, 1998). However, larger doses are may also be suitable for some patients, depending on the symptoms and the patient's general condition, etc.

In a preferred aspect of this invention, the $\alpha_1$-adrenergic antagonist is terazosin, which is administered orally to a male human in one daily dose of between about 5 mg and 10 mg, and saw palmetto extract, which is administered orally in one daily dose of about 320 mg.

The $\alpha_1$-adrenergic antagonist and the saw palmetto extract may be compounded into a single dosage form suitable for oral or parenteral administration. A tablet or capsule or caplets are particularly convenient forms for oral administration. Such compositions useful in the present invention are typically formulated with conventional pharmaceutical excipients, e.g., spray dried lactose and magnesium stearate into tablets or capsules for oral administration. One or more of the active substances, with or without additional types of active agents, can be worked into tablets or dragee cores by being mixed with solid, pulverulent carrier substances, such as sodium citrate, calcium carbonate or dicalcium phosphate, and binders such as polyvinyl pyrrolidone, gelatin or cellulose derivatives, possibly by adding also lubricants such a magnesium stearate, sodium lauryl sulfate, "Carbowax" or polyethylene glycols. Of course, taste-improving substances can be added in the case of oral administration forms.

As further forms of administration, one can use plug capsules, e.g. hard gelatin, as well as closed softgelatin capsules comprising a softener or plasticizer, e.g. glycerine. The plug capsules contain the active substance preferably in the form of a granulate, e.g. in mixtures with fillers, such as lactose, saccharose, mannitol, starches such as potato starch or amylopectin, cellulose derivatives or highly dispersed silicic acids. In soft gelatin capsules, the active substance is preferably dissolved or suspended in suitable liquids, such as vegetable oils or liquid polyethylene glycols.

In a preferred embodiment of this invention, the $\alpha_1$-adrenergic antagonist is dissolved or suspended in saw palmetto extract oil that is administered in the form of a softgelatin capsule. The $\alpha_1$-adrenergic antagonist and saw palmetto extract are combined in amounts that result in a desired concentration for the patient in need of such treatment. This is true of solid/solid, solid/oil, or other possible combinations of active ingredients.

The active ingredient components used in accordance with the present invention may also be formulated into once-a-day or even longer sustained release composition by conventional techniques well known in the art.

In place of oral administration, the active compounds may be administered parenterally. In such case, one can use a solution of the active substance, e.g., in sesame oil or olive oil.

The invention further provides a pharmaceutical-nutraceutical kit for treatment of BPH, said kit including two separate containers of different active ingredients which, when administered contemporaneously, result in a combination therapy in accordance with the invention. For instance, a first container may hold the $\alpha_1$-adrenergic antagonist in the preferred form (e.g., the form of a pill or softgelatin capsule), and a second container holds the saw palmetto in the preferred form (e.g., the form of a pill or softgelatin capsule). The first and second containers are then packaged together either by an external wrap, or by physically joining the first and second containers through, for example, plastic molding or other suitable means. The preferred form of each ingredient need not be the same, but can vary in accordance with the preferred mode of administration.

In one preferred aspect, the present invention provides an effective method of alleviating the symptoms of benign prostatic hyperplasia while concomitantly reducing prostate volume thereby lowering the risk of disease progression, urinary retention and the need for surgery.

To assist in determining the effect of the treatment, American Urologic Association Symptom Index (AUASI), urine flow rate and prostate volume are measured. Decreased AUASI score, improved flow rate, and reduction in prostate volume are indicative of successful treatment.

The prostate volume is estimated by digital rectal examination and/or by transrectal ultrasonography. Objective assessment of the effect of treatment is also measured by physical methods well known to those skilled in the art of urodynamics, as well as by physical examination.

While the invention has been described and illustrated with reference to certain particular embodiments thereof, those skilled in the art will appreciate that various changes, modifications and substitutions can be made therein without departing from the spirit and scope of the invention. For example, effective dosages other than the particular dosages as set forth herein above may be applicable as a consequence of variations in the responsiveness of the subject being treated for any of the indications for the compounds of the invention indicated above. Likewise, the specific pharmacological responses observed may vary according to and depending upon the particular active compound selected or whether there are present pharmaceutical carriers, as well as the type of formulation and mode of administration employed, and such expected variations or differences in the results are contemplated in accordance with the objects and practices of the present invention. It is intended, therefore, that the invention be defined by the scope of the claims which follow and that such claims be interpreted as broadly as is reasonable.

What is claimed is:

1. A method of treating a patient showing symptoms of benign prostatic hyperplasia, the method comprising:

administration of a therapeutically effective amount of a synthetic pharmacologic $\alpha_1$-adrenergic antagonist in synergistic combination with a therapeutically effective amount of a phytotherapeutic agent consisting of saw palmetto extract;

wherein the $\alpha_1$-adrenergic antagonist is administered to alleviate symptoms of benign prostatic hyperplasia, and the saw palmetto extract is administered to reduce the volume of the patient's prostate caused by the benign prostatic hyperplasia.

2. The method of claim 1, wherein the administration is oral.

3. The method of claim 1, wherein the administration is parenteral.

4. The method of claim 1, wherein the $\alpha_1$-adrenergic antagonist is selected from a group consisting of terazosin, doxazosin, and tamsulosin.

5. The method of claim 1, wherein the $\alpha_1$-adrenergic antagonist is compounded into a single oral unit with the saw palmetto extract.

6. The method of claim 5, wherein the single oral unit is a tablet.

7. The method of claim 5, wherein the single oral unit is a capsule.

8. The method of claim 1, wherein the $\alpha_1$-adrenergic antagonist is dissolved or suspended in saw palmetto extract oil.

9. The method of claim 8, wherein the dissolved or suspended $\alpha_1$-adrenergic antagonist is placed in a single oral softgelatin capsule.

10. The method of claim 1, wherein the $\alpha_1$-adrenergic antagonist is formed into a first single oral unit, and the saw palmetto is formed into a second single oral unit.

11. The method of claim 10, wherein a number of first single oral units are placed in a first container, and a number of the second single oral units are placed in a second container.

12. The method of claim 11, wherein the first and second containers are packaged together.

13. The method of claim 10, wherein the first and second single oral units are a tablet.

14. The method of claim 10, wherein the first and second single oral units are a capsule.

15. The method of claim 10, wherein the second single oral unit is a softgelatin capsule.

16. The method of claim 1, wherein the $\alpha_1$-adrenergic antagonist is terazosin, the terazosin being administered orally to the patient in one daily dose of between about 5 mg and 10 mg.

17. The method of claim 1, wherein the saw palmetto extract is administered orally to the patient in one daily dose of about 320 mg.

18. The method of claim 10, wherein binders and carriers are used in the first and second oral units to facilitate the administration of the $\alpha_1$-adrenergic antagonist and the saw palmetto extract.

* * * * *